United States Patent [19]
Giebeler, Jr.

[11] Patent Number: 5,123,740
[45] Date of Patent: Jun. 23, 1992

[54] STRAY LIGHT TRAP IN A MONOCHROMETER

[75] Inventor: Robert H. Giebeler, Jr., Cupertino, Calif.

[73] Assignee: Beckman Instruments, Inc., Fullerton, Calif.

[21] Appl. No.: 641,202

[22] Filed: Jan. 15, 1991

[51] Int. Cl.⁵ .............................................. G01J 3/18
[52] U.S. Cl. .................................. 356/331; 356/334
[58] Field of Search ................ 356/331, 332, 333, 334

[56] References Cited

U.S. PATENT DOCUMENTS

| | | | |
|---|---|---|---|
| 4,300,835 | 11/1981 | Schiemann et al. | 356/334 |
| 4,830,493 | 5/1989 | Giebeler | 356/328 |
| 4,919,537 | 4/1990 | Giebeler | 356/328 |
| 4,921,350 | 5/1990 | Giebeler | 356/320 |

OTHER PUBLICATIONS

Publication "Optical Black Surface" by Martin Marietta undated.

*Primary Examiner*—F. L. Evans
*Attorney, Agent, or Firm*—William H. May; P. R. Harder; Wen Liu

[57] ABSTRACT

A monochrometer having a stray light trap which substantially directs stray light away from light of wavelength of interest and/or absorb the stray light so as to substantially reduce the stray light component in the light of interest. The monochrometer has internal surfaces each having one of several optical characteristics.

18 Claims, 4 Drawing Sheets

STRAY LIGHT TRAP IN A MONOCHROMETER

BACKGROUND OF THE INVENTION

1. Field of the Invention

The present invention relates to the production of monochromatic light, and in particular relates to a monochrometer for use in an analytical centrifuge.

2. Description of Related Art

The following United States Patents are incorporated by reference herein: U.S. Pat. Nos. 4,830,493; 4,919,537; and 4,921,350. These patents were issued to the inventor of the present invention and were commonly assigned to Beckman Instruments, Inc., the assignee of the present invention. The patents describe monochrometers designed for use in analytical centrifuges.

A monochrometer is a device used to supply a collimated beam of light having some desired, narrow range of wavelengths. A monochrometer typically has the following component parts: (1) an entrance slit with a source of radiation of a wide range of wavelengths; (2) a prism or diffraction grating dispersing the incident radiation into a continuous spectrum of wavelengths; (3) some mechanism to rotate the prism or grating so that the desired spectrum of radiation is obtained; and (4) an exit slit selectively isolating a narrow band of wavelengths. For spectrophotometry studies, a detector is positioned at the monochrometer exit for detecting the radiation antennuation of a sample placed between the exit and the detector. Appropriate signal amplification circuit is provided in conjunction with the detector.

Referring to FIG. 1, the arrangement of a prior art monochrometer in an analytical centrifuge as described in the patents is briefly summarized. The centrifuge 10 comprises a rotor 12 driven to rotate about an axis by a motor 14. The rotor 12 has several sample cells 16 having transparent windows to allow a monochromatic light beam from the monochrometer 18 to be directed vertically through each sample cell 16 as the cells rotate pass the beam. A detector 20 is positioned below the rotor 12 in line with the beam. As illustrated in FIG. 1, the monochrometer 18 comprises a light tube 22 folded along its length. Light from a source 24 is directed through the light tube 22 to a mirror 26 having diffraction rulings. The mirror 26 can be tilted to direct light of a particular spectrum range through the remaining length of the light tube towards the rotor. A slit (not shown) at the tube exit select a narrow wavelength band from the spectrum for transmission through the sample cells 16.

The prior art monochrometer has certain limitations in obtaining a true monochromatic beam of light. Specifically, the diffraction grating mirror reflects light at wavelengths other than that of interest, including higher order wavelengths. The light exiting through the slit at wavelengths other than that of interest is often referred to as "stray light". The stray light is scattered at various angles which reflects or scatters off the internal walls of the light tube 22. Some of the reflected or scattered stray light is incident back to the diffraction grating mirror 26 which causes additional diffractions at the wrong wavelengths or is mixed in with the monochrometer output. The reliance upon a monochrometer output of a known wavelength of light is however critical to the results of the spectrophotometric study.

SUMMARY OF THE INVENTION

The present invention is directed to a monochrometer which substantially reduces the stray light component in the monochrometer output. The monochrometer has internal wall features that are designed to capture stray light, so that the stray light does not reflect or scatter back to the diffraction grating or mix in with the monochrometer output.

According to the present invention, surfaces with different optical characteristics are strategically positioned along the internal walls of the light tube in a manner which will either absorb incident stray light and/or reflect stray light in a direction away from the diffraction grating and the exit of the monochrometer. In the described embodiment, light absorbing surfaces with three different characteristics are provided. Some of the surfaces are very smooth reflective semi-absorbing, some are semi-smooth reflective semi-absorbing, and some are rough scattering, highly absorbing. The placements of the surfaces at selected locations and orientations causes stray light to be trapped away from the diffraction grating and the exit of the monochrometer.

DETAILED DESCRIPTION OF THE ILLUSTRATED EMBODIMENT

The following description is of the best presently contemplated mode of carrying out the invention. This description is made for the purpose of illustrating the general principles of the invention and should not be taken in a limiting sense. The scope of the invention is best determined by reference to the appended claims.

Figure 1:
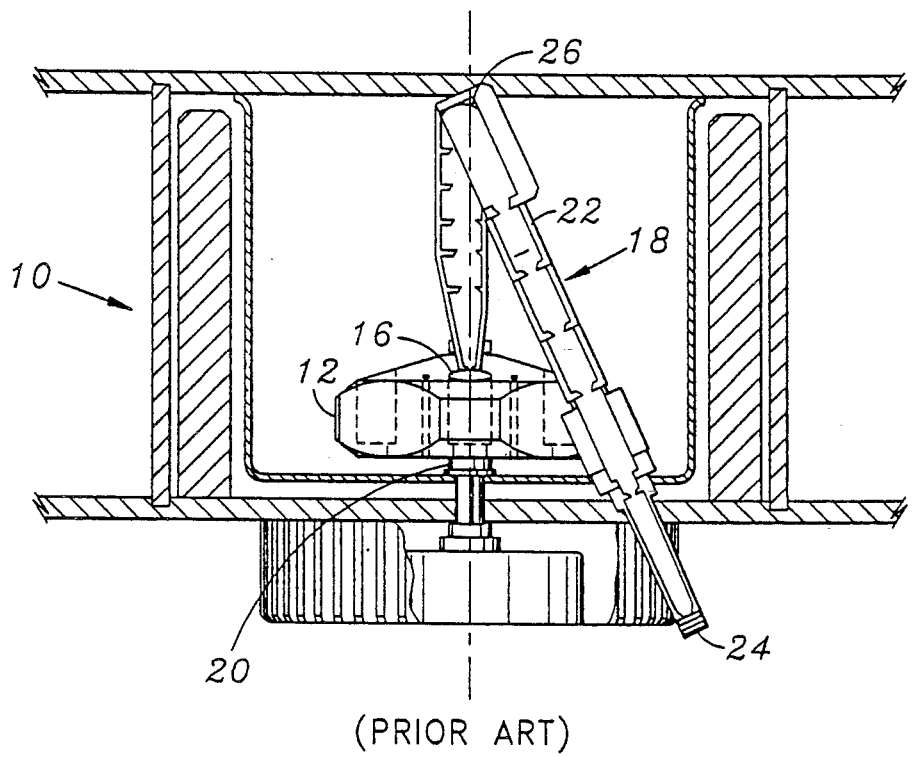
FIG. 1 depicts an analytical centrifuge having a prior art monochrometer.
Figure 2:
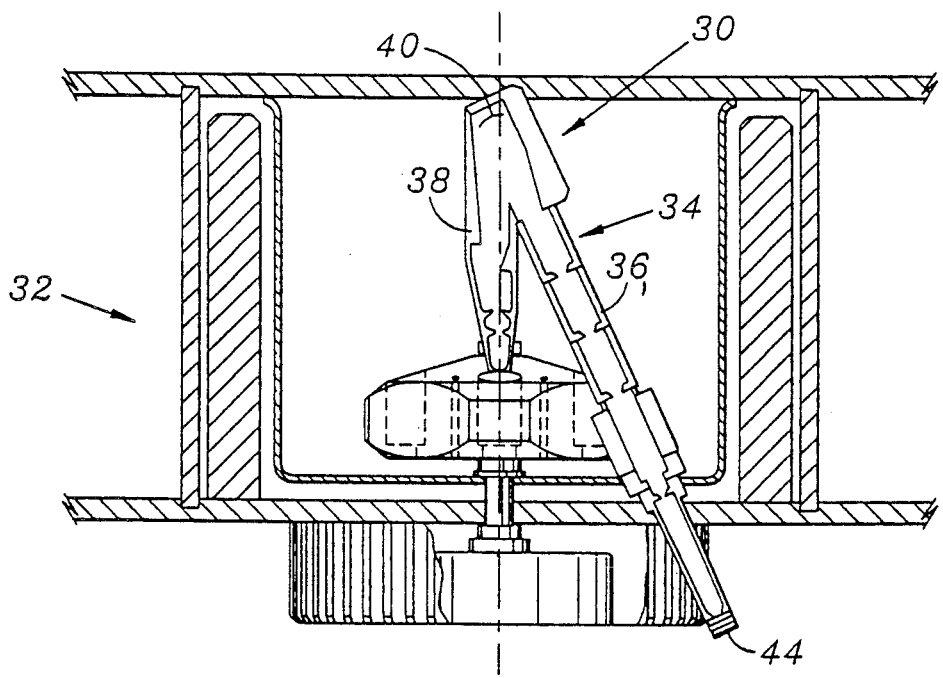
FIG. 2 illustrates an analytical centrifuge having a monochrometer in accordance with one embodiment of the present invention.

Referring to FIG. 2, the installation of a monochrometer 30 according to one embodiment of the present invention in an analytical centrifuge 32 is illustrated. The set up of the monochrometer 30 with respect to the centrifuge 32 is similar to those described in U.S. Pat. Nos. 4,830,493; 4,919,537 and 4,921,350 which have been incorporated by reference herein. However, the design of the light tube 34 of the monochrometer 30 is significantly different in that the light tube 34 is structured to trap stray light.

Figure 3:
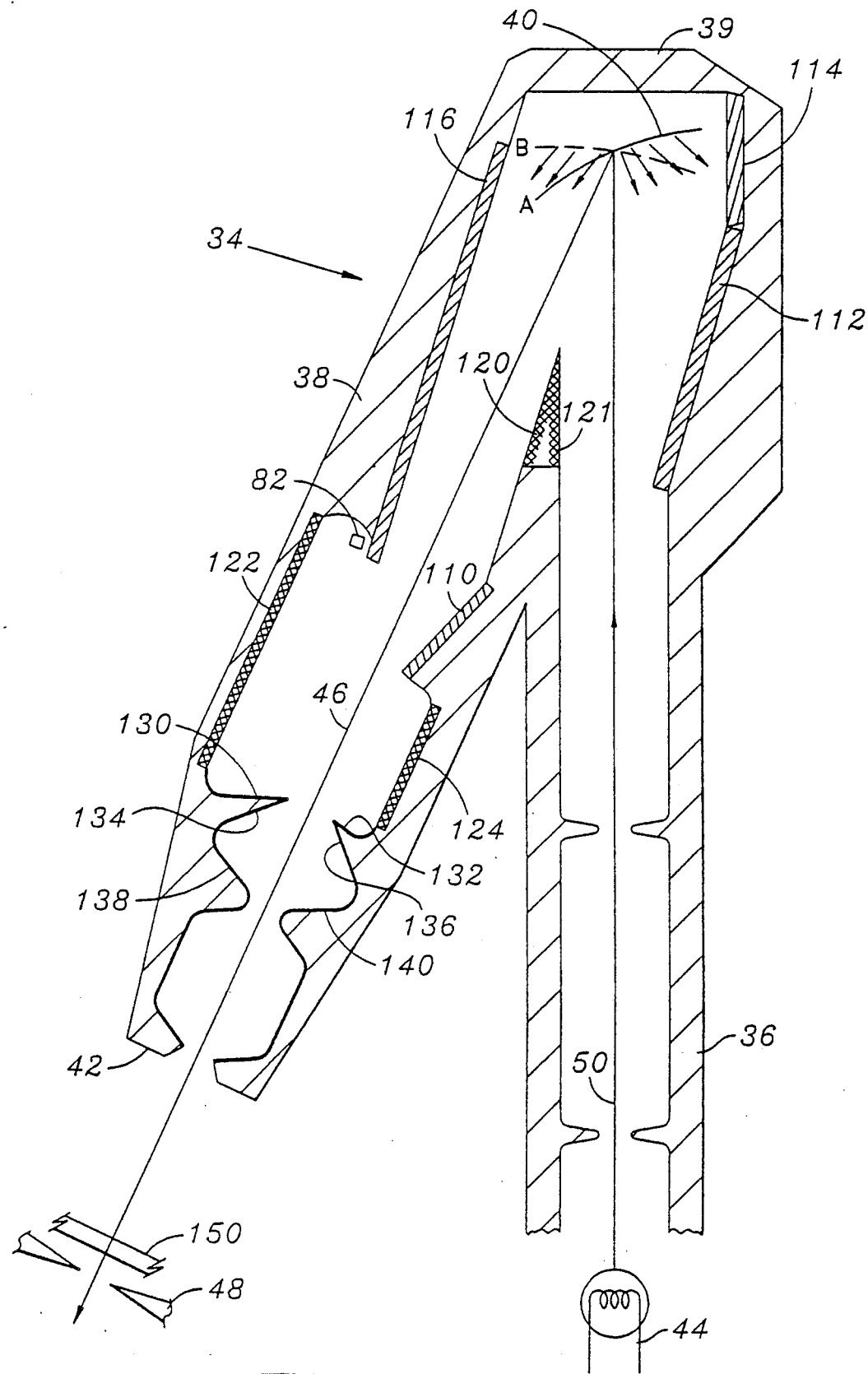
FIG. 3 is an internal view of the monochrometer showing the locations of the surfaces with different optical characteristics.

Referring to FIG. 3, the inside of the light tube 34 of the monochrometer 30 is illustrated in simplified form. The light tube 34 is made up of two segments 36 and 38 coupled at an elbow 39 in which a diffraction mirror 40 is disposed. Some structures have been omitted for clarity, the details of which are found in U.S. Pat. Nos. 4,830,493; 4,919,537; and 4,921,350. Similar to the monochrometers described in the patents, the mirror 40 has diffraction grating ruled on its surface. The mirror 40 is shaped about one axis (along the plane of FIG. 3) for the generation of collimated lights. The cross-section of the segment 36 is round and that of the segment 38 is rectangular. Incident light 50 from a light source 44 directed at the mirror 40 diffracts into coherent lights of different wavelengths including 0, 1, and higher order components. About another axis (perpendicular to the plane of FIG. 3), the mirror 40 is provided with a varying curvature and varying spaced rulings so that tilting of the mirror 40 selectively directs light of a particular wavelength range through the exit end 42 of the light tube segment 38 towards the sample. An exit slit 48 is used to selectively isolate a narrow band of the light emerging from the exit end 42. A motor coupled with a gear mechanism (not shown) are provided to tilt the mirror 40 between two extreme positions A and B as shown in FIG. 3.

Because the mirror 40 diffracts light at wavelengths not of interest (stray light) in different directions parallel to the plane of FIG. 3, the internal structure of the light tube 34 of the present invention is designed so that it does not reflect or scatter back stray light to the mirror 40 and cause re-diffraction at the wrong wavelength. The internal structure is designed also to prevent stray light from mixing with the exit light. This results in the light at the wavelength of interest passing through the monochrometer to have very little stray light. Typically, the wavelength of interest is in the 1 or −1 order. The zero order wavelength is typically not used for spectrophotometric studies because of too high intensity and polychromatic. Higher order wavelengths are also not of interest because of possible confusion (overlap) with the primary order wavelengths.

To accomplish stray light trapping, the inner surfaces of the light tube 34 is finished or otherwise lined with materials of certain optical characteristics. In the illustrated embodiment, the surfaces have one of three characteristics: (1) very smooth reflective semi-absorbing, (2) semi-smooth reflective semi-absorbing, and (3) rough scattering, highly absorbing. The first type of surface can be obtained by lining the inside of the light tube 34 using absorptive glass, Cat-A-Lac Gloss or Parson's Black surfaces. The second type of surface can be obtained by black anodising the smooth machined inside surface of the light tube 34. The third type of surface can be obtained by coating the inside surface of the light tube 34 using a special "optical black" coating developed by Martin Marietta Aerospace Corp. It has been found that for the three types of surfaces, light back scatter ten times less for the first type of surface as compared to the third type of surface, and the third type is ten times less than the second type of surface. The first type of surface, however, does have the highest reflected intensity at the complementary angle.

The surfaces having the respective characteristics are strategically positioned along the inner walls of the light tube 34 as shown in FIG. 3. Generally, the surfaces nearer the mirror 40 has the first characteristic. Further down the segment 38 of the light tube 34 are positioned the surfaces having the third characteristic. Surfaces having the second characteristic are found near the exit end of the segment and any other surfaces not having the first and second characteristics. Because the diffracted light from the mirror is collimated parallel to the plane of FIG. 3, the side walls (parallel to plane of FIG. 3) of the rectangular section of the segment 38 (including the elbow portion having surfaces 112 and 114) are exposed to very little stray light and thus can be left as machined surfaces or made to possess the second characteristic. Specifically, the surfaces (flat) 110, 112, 114 and 116 with a high view factor of the diffraction grating mirror 40 (i.e. ratio of direct view to the mirror and direct view to other structures), or that receive zero order light, have the first characteristic so as to minimize scattering and provide controlled reflection, as will become clear in the discussion below. For the first type of surfaces, about 10% of incident light is reflected, 0.5% of incident light is diffusely scattered, and the rest of the light is absorbed. Surfaces 120, 121, 122 and 124 which do not have a high view factor to the diffraction grating mirror (i.e. substantially not in direct view of the mirror) and which receives light reflected from other surfaces, have the third characteristic. Such surfaces absorb reflected light and/or diffusely scatter light but not to the mirror because of the absence of view factor to the mirror. The general characteristics of the third type of surfaces are reflectance of less than 0.5% over the entire visible region (400–700 nm) and less than 0.8% from 300 to 900 nm, and light absorbance over a large spectrum (0.27 to 20 microns). Finally, the rest of the surfaces (e.g. 130, 132 etc. near the exit end 42 of the segment 38) which are exposed to light very near the wavelength of interest have the second characteristic.

As can be seen in FIG. 3, along the second segment 38 of the light tube, some of the surfaces (e.g. 110, 116) protrude towards the axis of the segment 38. The protruding surfaces defines a clearance for passage of light 46 of the desired wavelength reflected from the diffraction mirror 40.

The stray light trapping mechanism of the surfaces will be described separately in FIGS. 4 and 5. As mentioned, the zero order white light component of stray light is of particular concern because of its high intensity. It is noted that the particular orientation of the mirror 40 between positions A and B (FIG. 3) would not affect the analysis of the stray light trapping mechanism. The light rays shown in the figures are only representative of the paths of light reflected from the mirror 40. The analysis is applicable to all order of light rays reflected from the mirror 40 at any mirror orientation.

Figure 4:
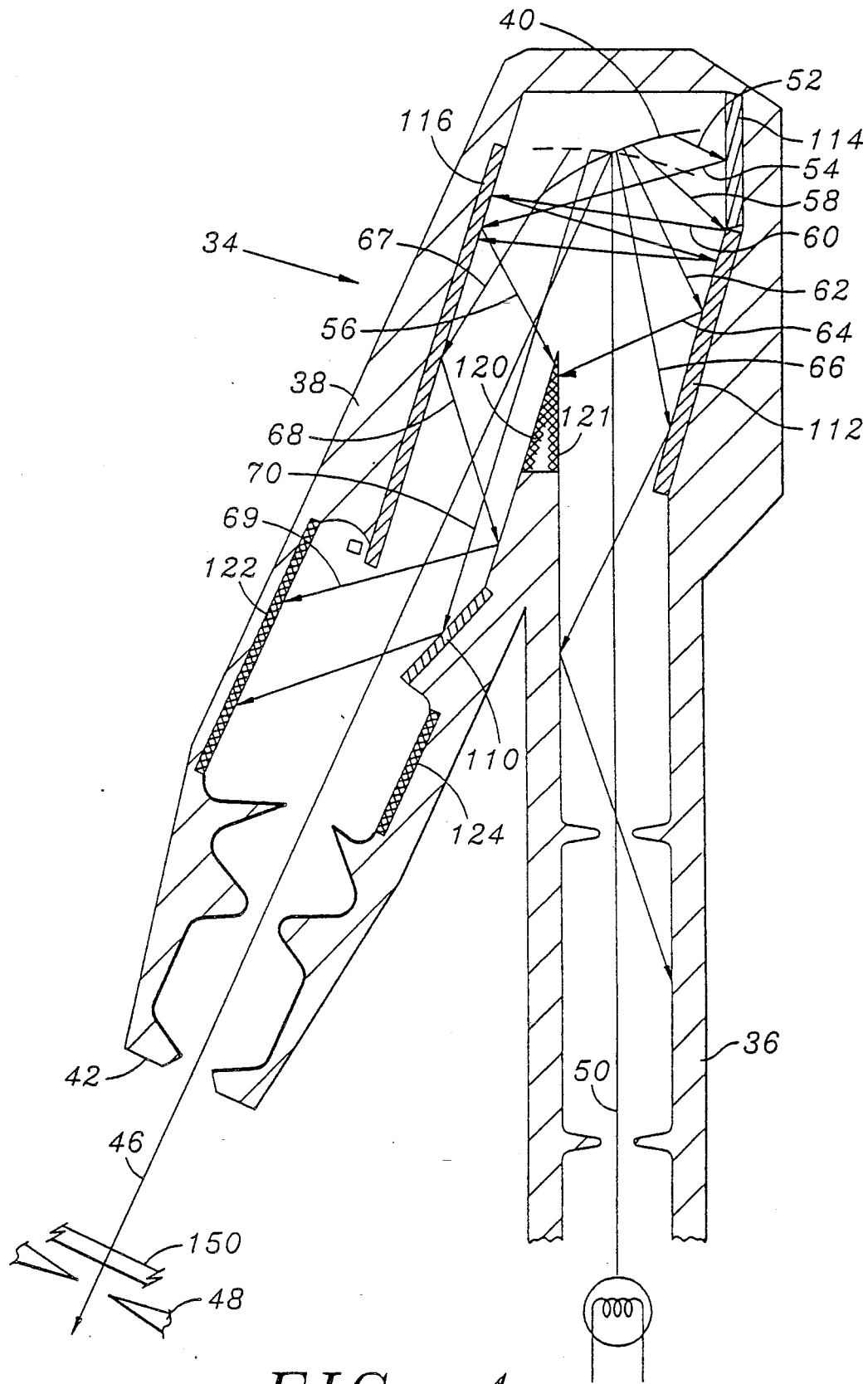
FIG. 4 illustrates stray light trapping in a region near the diffraction mirror.

Referring to FIG. 4, the worst case of stray light having zero order white light component is shown. The zero order ray 52 reflects off of surface 114 which is positioned such that the reflected ray 54 misses the mirror 40 before reaching surface 116. The ray 54 is reflected off of surface 116 in a ray 56 towards surface 120. About 10% of incident light is reflected at the surfaces 114 and 116. About 0.5% of incident light on surfaces 114 and 116 is diffusely scattered. The rest of the incident light is absorbed by these surfaces. Thus, the ray 56 is about 1% of the incident ray 52 diffracted from the mirror 40. This 1% of light after being absorbed by highly absorbing surface 120 will have very little light intensity. Other light rays from mirror 40 directed at surface 114 will follow a somewhat similar path leading to a substantial reduction of intensity.

The ray 58 which is directed at surface 112 just beyond surface 114 is reflected along ray 60 and clears the mirror 40 before being reflected at surface 116. The reflected ray continues to be reflected between the surfaces 112 and 116, wherein the intensity of the stray light is reduced by 90% each time it is reflected off the surfaces 112 and 116. The surface 112 is set at a slightly diverging angle to surface 116, so that the multiple reflections do not converge back to the mirror. The transition point between surfaces 114 and 112 is determined by letting the ray 58 just clear the mirror. Other rays from the mirror 40 to the surface 112 will also experience multiple reflections, except beyond ray 62 which is reflected at surface 112 to the surface 121 (ray 64). The high absorbing surface 121 substantially absorbs the intensity of ray 64. Ray 66 is reflected at surface 112 to the inner walls of the light tube segment 36. The multiple reflections occurring in the segment will substantially diminish the stray light intensity.

Stray light 67 from the mirror 40 is reflected at surface 116 to surface 121 (ray 68) and to surface 122 (ray 69) which is substantially absorbed. Stray light ray 70 is reflected at surface 110 to surface 122. Any diffuse scattering from surface 122 does not affect the mirror 40 since surface 122 does not have a view factor to the mirror 40. In any event, the diffusely scattered stray light from surface 122 is of low intensity which is further diminished when the scattered light reaches the adjacent light absorbing surfaces. To maintain the clarity of FIG. 4, the reflected or scattered low intensity light rays are not shown in the figure.

Figure 5:
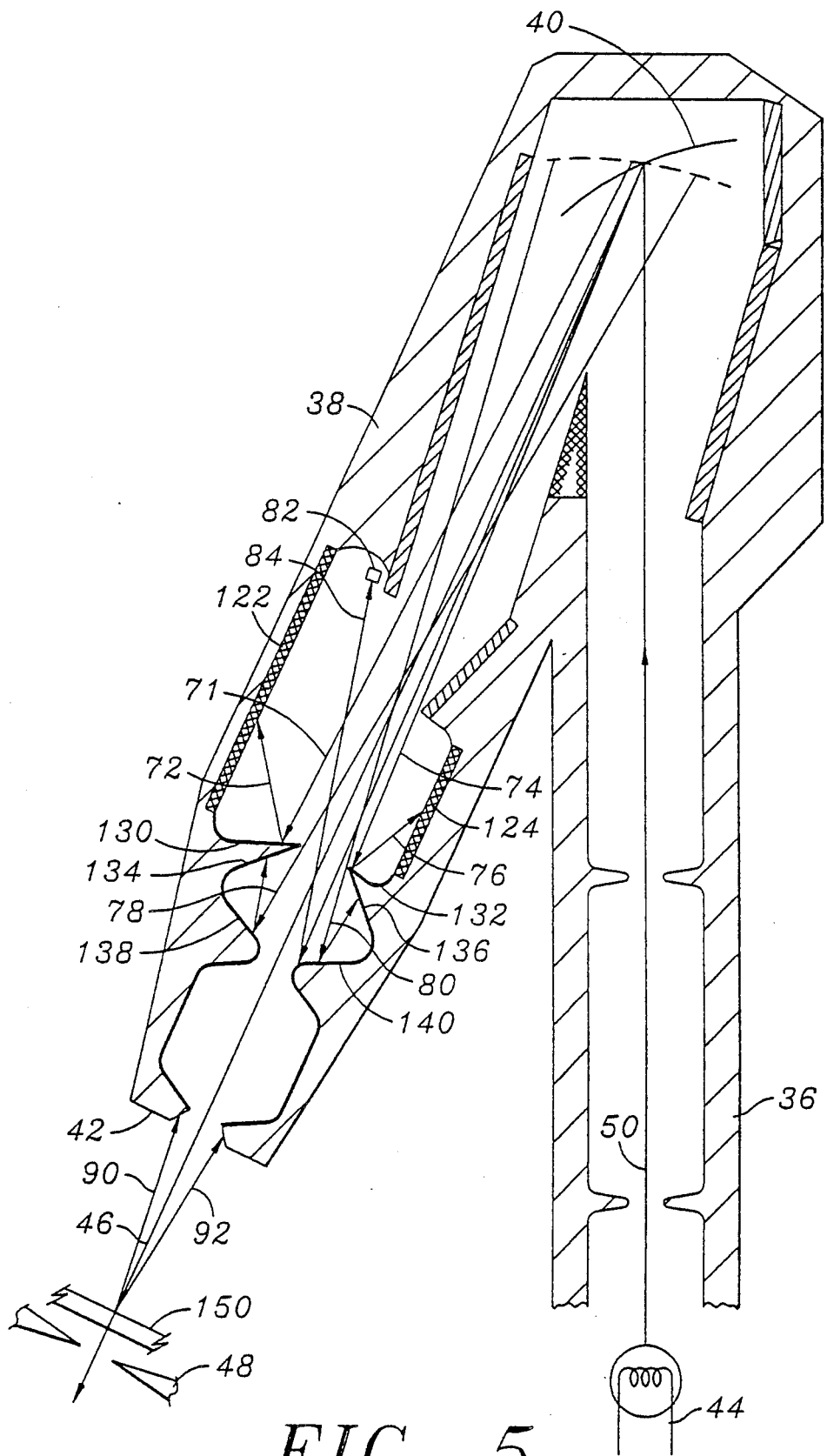
FIG. 5 illustrates stray light trapping in a region near the monochrometer exit.

Referring now to FIG. 5, the stray light trapped at the lower end of the segment 38 is now discussed. Ray 71 from mirror 40 is reflected at surface 130 to surface 122 where the light is substantially absorbed. Similarly, ray 74 is reflected at surface 132 to surface 124 (ray 76) and absorbed. The light rays 78 and 80 which are very near the wavelength of interest (ray 46) are respectively reflected at surfaces 138 and 140 to surfaces 134 and 136, respectively. The protrusions of surfaces 134 and 136 keep light from reflecting back to the diffraction mirror 40. In the configuration shown in FIG. 5, an incident light detector 82 can be placed at the shoulder defined between surfaces 116 and 122 to receive light ray 84 reflected from surface 140. This reflected light provides a reference light intensity at a wavelength very close to the desired wavelength of ray 46 for the spectrophotometric analysis. The protruding corners of surfaces 134, 136, 138 and 140, and corners 142 and 144 shield the mirror 40 from the light rays 90 and 92 reflected from the window 150 of the sample cell in the rotor. These corners also shields the incident detector 82 from light reflected from the window 150.

The exact dimensions of the internal wall structure can be derived without undue experimentation given the described functions of each of the surfaces.

While the invention has been described with respect to the preferred embodiments in accordance therewith, it will be apparent to those skilled in the art that various modifications and improvements may be made without departing from the scope and the spirit of the invention. For example, the surfaces may be substituted with surfaces of other characteristics which can also accomplish the same stray light trapping tasks e.g. substituting the third type of surfaces for the second type, except that the third type of surfaces are more expensive to make. Accordingly, it is to be understood that the invention is not to be limited by the specific illustrated embodiments, but only by the scope of the appended claims.

I claim:

1. A monochrometer comprising:
   a body having internal walls defining a generally elongated conduit for passage of light, the conduit having first and second ends;
   a light source directing light through the conduit from the first end;
   dispersion means for dispersing light from the light source into a spectrum of a range of wavelengths, said dispersion means is disposed within the conduit and directs light of wavelength of interest through the second end;
   the internal walls about the dispersion means and leading to the second end include a first portion and a second portion, the first and second portions having surfaces of different absorptive and reflective characteristics and being positioned in a manner such that the first portion is substantially in direct view of the dispersion means and the second portion is substantially not in direct view of the dispersing means and such that the first portion reflects stray light in directions substantially away from the dispersion means so as to substantially prevent stray light from reflecting back to the dispersion means and the second portion absorbs the stray light reflected by the first portion.

2. A monochrometer as in claim 1 wherein the surfaces on the first portion have reflective and absorbing characteristics and the surfaces on the second portion have absorbing and scattering characteristics.

3. A monochrometer as in claim 2 wherein the first portion is positioned close to the dispersion means and most of the second portion is positioned further from the dispersion means than the first portion and closer towards the second end of the conduit.

4. A monochrometer as in claim 3 wherein the internal walls of the conduit further include a third portion at the second end which has surfaces that are semi-absorbing and semi-smooth reflective.

5. A monochrometer comprising:
   a body defining a generally elongated conduit for passage of light;
   dispersion means disposed within the conduit for dispersing light from an inlet end of the conduit into a spectrum of a range of wavelengths and directing light of a wavelength of interest through an exit end of the conduit;
   a portion of the conduit adjacent the dispersion means including surfaces that are substantially in direct view of the dispersion means and that have reflective and absorbing characteristics whereby the surfaces are positioned in a manner such that stray light is reflected in directions substantially away from the dispersion means so as to substantially prevent stray light from reflecting back to the dispersion means, and
   a portion of the conduit further from the dispersion means than the first portion and closer to the exit end including surfaces that are substantially not in direct view of the dispersion means and that have absorbing and scattering characteristics, said surfaces of the second portion are positioned in a manner such that the stray light reflected from the first portion is absorbed by the second portion.

6. A monochrometer as in claim 5 wherein the conduit further includes a third portion at the exit end which has surfaces that are semi-absorbing and semi-smooth reflective.

7. A centrifuge comprising:
   a rotor having a sample cell for holding a sample for centrifugation;
   a monochrometer configured to provide substantially monochromatic light of a particular wavelength through the sample cell, the monochrometer comprising:
   a body having internal walls defining a generally elongated conduit for passage of light, the conduit having first and second ends;

a light source directing light through the conduit from the first end;

dispersion means for dispersing light from the light source into a spectrum of a range of wavelengths, said dispersion means is disposed within the conduit and directs light of wavelength of interest through the second end;

the internal walls adjacent the dispersion means and leading to the second end include a first portion and a second portion, the first and second portions having surfaces of different absorptive and reflective characteristics and being positioned in a manner such that the first portion is substantially in direct view of the dispersion means and the second portion is substantially not in direct view of the dispersion means and such that the first portion reflects stray light in directions substantially away from the dispersion means so as to substantially prevent stray light from reflecting back to the dispersion means and the second portion absorbs the stray light reflected by the first portion.

8. A centrifuge as in claim 7 wherein the surfaces on the first portion have reflective and absorbing characteristics and the surfaces on the second portion have absorbing and scattering characteristics.

9. A centrifuge as in claim 8 wherein the first portion is positioned close to the dispersion means and most of the second portion is positioned further from the dispersion means than the first portion and closer towards the second end of the conduit.

10. A centrifuge as in claim 9 wherein the internal walls of the conduit further include a third portion at the second end which has surfaces that are semi-absorbing and semi-smooth reflective.

11. A centrifuge comprising:

a rotor having a sample cell for holding a sample for centrifugation;

a monochrometer configured to provide substantially monochromatic light of a particular wavelength through the sample cell, the monochrometer comprising:

a body defining a generally elongated conduit for passage of light;

dispersion means disposed within the conduit for dispersing light from an inlet end of the conduit into a spectrum of a range of wavelengths and directing light of a wavelength of interest through an exit end of the conduit;

a portion of the conduit adjacent the dispersion means including surfaces that are substantially in direct view of the dispersion means and that have reflective and absorbing characteristics whereby the surfaces are positioned in a manner such that stray light is reflected in directions substantially away from the dispersion means so as to substantially prevent stray light from reflecting back to the dispersion means, and a portion of the conduit further from the dispersion means than the first portion and closer to the exit end including surfaces that are substantially not in direct view of the dispersion means and that have absorbing and scattering characteristics, said surfaces of the second portion are positioned in a manner such that the stray light reflected from the first portion is absorbed by the second portion.

12. A centrifuge as in claim 11 wherein the conduit further includes a third portion at the exit end which has surfaces that are semi-absorbing and semi-smooth reflective.

13. A monochrometer comprising:

a light tube which comprises an inlet segment and an outlet segment coupled at a hollow elbow;

a light source;

dispersion means disposed within the elbow for dispersing light entering the elbow from the inlet segment into a spectrum of a range of wavelengths and directing light of a wavelength of interest through the outlet segment;

said elbow including internal surfaces positioned substantially in direct view of the dispersion means, said surfaces being positioned with respect to the dispersion means and having a surface characteristic that reflects stray light in directions substantially away from said dispersion means;

said outlet segment including internal surfaces which are recessed such that they are substantially not in direct view of said dispersion means, said outlet segment surfaces having a surface characteristic that absorbs the reflected stray light from said elbow surfaces;

whereby the positions and surface characteristics of the elbow and outlet segment surfaces prevent stray light from reaching said dispersion means.

14. A monochrometer as in claim 13 wherein the surface characteristic of said elbow surfaces is reflective and absorbing and the surface characteristic of said outlet segment surfaces is absorbing and scattering.

15. A monochrometer as in claim 14 wherein the outlet segment further includes internal surfaces having semi-absorbing and semi-reflective characteristics at an exit end of the outlet segment.

16. A centrifuge comprising:

a rotor having a sample cell for holding a sample for centrifugation;

a monochrometer configured to provide substantially monochromatic light of a particular wavelength through the sample cell, the monochrometer comprising:

a light tube which comprises an inlet segment and an outlet segment coupled at a hollow elbow;

a light source;

dispersion means disposed within the elbow for dispersing light entering the elbow from the inlet segment into a spectrum of a range of wavelengths and directing light of a wavelength of interest through the outlet segment;

said elbow including internal surfaces positioned substantially in direct view of the dispersion means, said surfaces being positioned with respect to the dispersion means and having a surface characteristic that reflects stray light in directions substantially away from said dispersion means;

said outlet segment including internal surfaces which are recessed such that they are substantially not in direct view of said dispersion means, said outlet segment surfaces having a surface characteristic that absorbs the reflected stray light from said elbow surfaces;

whereby the positions and surface characteristics of the elbow and outlet segment surfaces substantially prevent stray light from reaching said dispersion means.

17. A centrifuge as in claim 16 wherein the surface characteristic of said elbow surfaces is reflective and absorbing and the surface characteristic of said outlet segment surface is absorbing and scattering.

18. A centrifuge as in claim 17 wherein the outlet segment further includes internal surfaces having semi-absorbing and semi-reflective characteristics at an exit end of the outlet segment.

* * * * *